United States Patent [19]
Drury et al.

[11] Patent Number: 4,494,479
[45] Date of Patent: Jan. 22, 1985

[54] SLIDE PREPARATION APPARATUS

[75] Inventors: F. Robert Drury, Lexington; Marshall D. Graham, Framingham, both of Mass.

[73] Assignee: Coulter Electronics, Inc., Hialeah, Fla.

[21] Appl. No.: 459,045

[22] Filed: Jan. 19, 1983

Related U.S. Application Data

[63] Continuation-in-part of Ser. No. 434,378, Oct. 14, 1982.

[51] Int. Cl.³ ............... B05C 17/10; B05C 11/04; B05C 13/02
[52] U.S. Cl. .................. 118/120; 118/100; 118/500; 118/415; 15/104 S
[58] Field of Search ........... 118/100, 120, 206, 207, 118/401, 500, 413, 415, 108; 427/2; 206/456; 15/104 S; 101/123

[56] References Cited

U.S. PATENT DOCUMENTS

| 2,881,698 | 4/1959 | Graham | 101/123 |
| 4,359,013 | 11/1982 | Prevo | 118/100 |
| 4,392,450 | 7/1983 | Prevo | 118/120 |

Primary Examiner—Norman Morgenstern
Assistant Examiner—Robert J. Steinberger, Jr.
Attorney, Agent, or Firm—Silverman, Cass & Singer, Ltd.

[57] ABSTRACT

A portable, manually operable device for preparing a monolayer film of a biological fluid sample or the like on a slide for microscopic examination. Said device includes a base for retaining the slide thereon and a spreader manually movable linearly relative to the base and slide in a pass which spreads a sample of the fluid on the slide into such a monolayer. Preferably, the spreader is constructed to be disposable.

10 Claims, 5 Drawing Figures

U.S. Patent  Jan. 22, 1985  4,494,479
FIG. 1
FIG. 2
FIG. 3
FIG. 4
FIG. 5
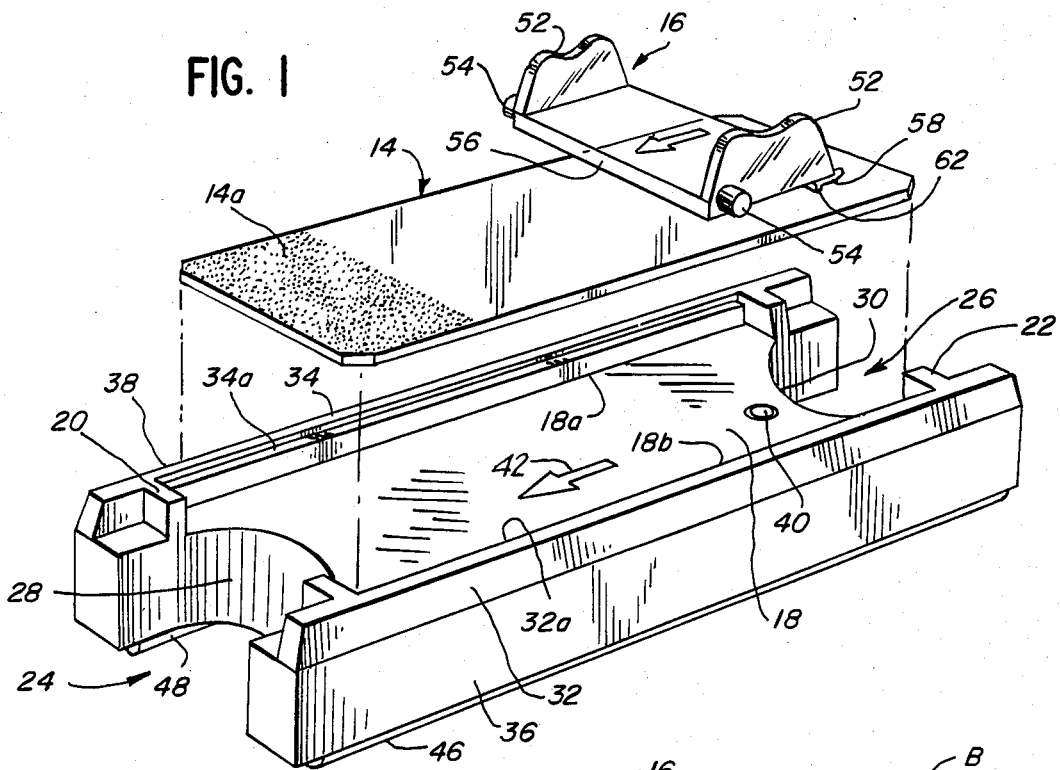
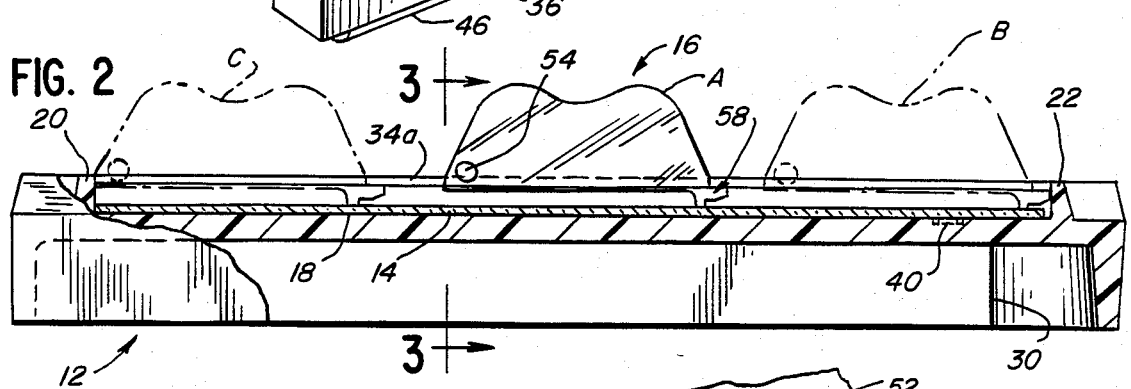
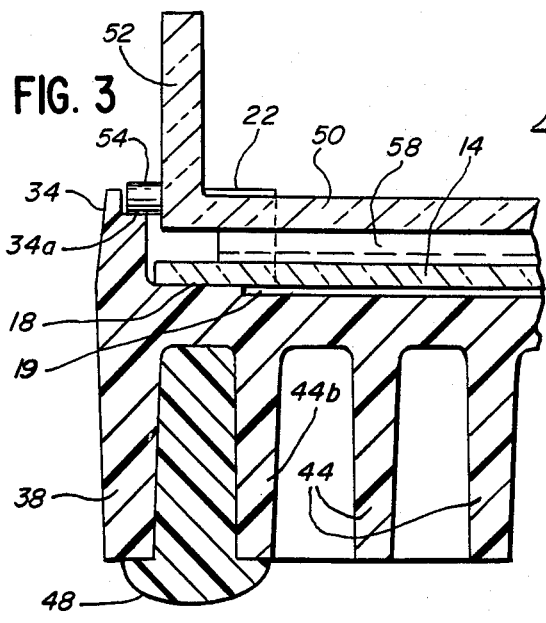
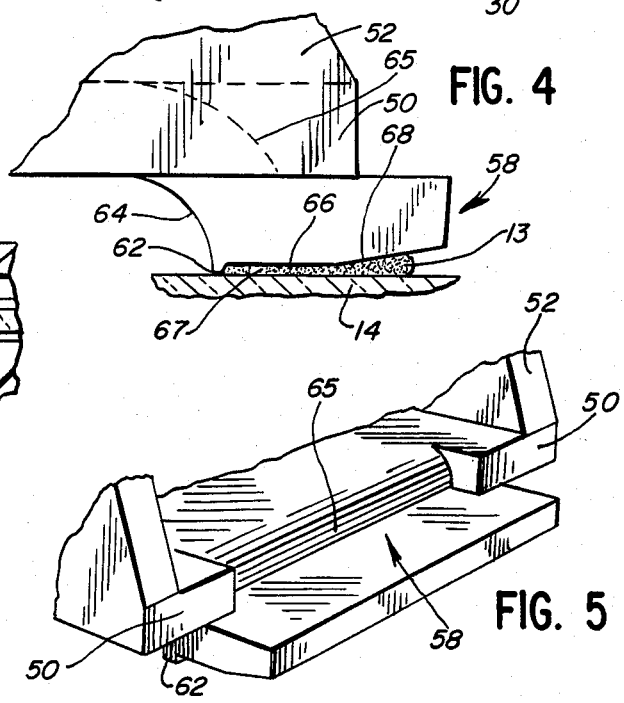

SLIDE PREPARATION APPARATUS

This is a continuation-in-part application of Ser. No. 434,378 filed Oct. 14, 1982 and owned by a common assignee.

BACKGROUND OF THE INVENTION

This invention generally relates to apparatus for the preparation of a fluid sample upon a slide for microscopic analysis, and more particularly, to improved apparatus for supporting the slide and spreading the sample thereon.

Prior art devices such as those described in U.S. Pat. No. 4,359,013 have employed a base on which a slide to be stained is supported flat on a support surface thereof. A spreader is manually movable linearly relative to the base and engaging the surface of the slide with appreciable downward force so that the fluid sample can be spread over the slide to form a so-called "monolayer" of the sample. The spreader is intended to be disposable after each use thereof. Typically, a blood sample is spread into a monocellular layer on the slide which can then be microscopically examined for blood cell differential screening.

Several deficiencies exist in such prior art devices. As structured, the spreader frictionally engaged said support surface so that it formed grooves or ruts in the support surface of the base after multitudinous passes. Eventually, irregularities in the path of the movement of the spreader relative to the slide actually interfered with uniformity of spreading of the sample and thereby prevented achieving the desired monocellular layer consistently with the same base which was not intended to be disposable. Also, the base tended to deform or flex downwardly because of the necessity to press downwardly on the spreader when making the monolayer. This deformation or flexing contributed to breakage of the slides on occassion as well as possible non-uniformity in monolayer spread of the sample on the slide.

In the referenced application Serial No. 434,378, the sample spreader rides entirely upon the slide in a linear movement for preparing the sample smear. Therefore, grooving in the slide support surface of the base is avoided. However, the use of a slide having a textured or "frosted" end area to accept written identification has sometimes led to interruption of the smear when the legs of the spreader arrive at the abrupt line of transition between the smooth glass and the frosted end area. The resulting interruption or "banding" may result in an insufficient extent of the smear for proper microscopic examination by automatic instruments. Such smear banding is eliminated by the apparatus of the described invention herein.

SUMMARY OF THE INVENTION

Slide smear apparatus for preparing a monolayer film of a biological fluid sample on a slide includes a base and a manually movable spreader which is disposable. The slide is to be supported flat on a bed surface of the base. The base has a pair of side walls upstanding along opposed longitudinally extending side edges thereof between which said slide bed is provided. Said side walls have elongate ramp or bearing formations spaced above the bed in a parallel horizontal plane. The spreader has a pair of outwardly protruding projections or trunnions which are coplanar and constructed and arranged to ride on said ramp or bearing formations with the spreader positioned between said side walls. The spreader has a depending blade member for engaging the slide to form said monolayer film when the spreader is moved linearly along said ramp formations riding on said pins or trunnions. Accordingly, the linear distance or elevation of the ramp formations above the slide bed as well as the spacing of the axes of said pins or trunnions relative to said slide base are coordinated with the thickness of the slide to assure that said blade member engages the slide for forming the film during linear movement of the spreader across the base.

BRIEF DESCRIPTION OF THE DRAWING

FIG. 1 is an exploded, perspective view of a slide preparation device embodying this invention;

FIG. 2 is a side elevational view of said apparatus assembled for operation with portions broken away to show details and illustrating diagrammatically, in part, three positions of the spreader riding on the slide in the preparation of the monolayer film thereon;

FIG. 3 is a sectional view taken along lines 3—3 of FIG. 2 and in the direction indicated generally;

FIG. 4 is a fragmentary view taken on FIG. 2 and enlarged to illustrate a broken outline position of the spreader at the right side end of FIG. 2 and with a fluid sample located for being spread when the spreader is moved to the left in FIG.2;

FIG. 5 is a fragmentary, perspective view of the blade end of the spreader of FIG. 4.

DESCRIPTION OF THE PREFERRED EMBODIMENT

Referring to FIG. 1, the slide preparation device embodying the invention is designated generally by reference character 10. Apparatus 10 includes a base 12 for supporting a typical laboratory slide 14 upon which a monolayer film of biological fluid is to be formed for microscopic analysis. One specialized use of apparatus 10 contemplates of sample of blood 13 being spread manually upon slide 14 by a spreader 16 in a linear movement so as to distribute the blood in a monolayer or monocellular film upon the slide 14, as more fully described hereinafter.

Base 12 is fabricated preferably from a rigid and tough, but easily molded material, for example crylonitrile-butadiane-styrene resin (ABS). The resin may contain a self-lubricating component, for example, approximately 10 weight percent polytetrafluoroethylene, in order to prevent frictional wear on the rails of the base 12 by the movement of the spreader 16 as described hereinafter. Based 12 is a generally rectangular structure having a horizontal, upper surface 18 which forms a bed upon which slide 14 is supported. The slide is placed between a pair of positioning posts 20 and 22 located adjacent respective ends 24 and 26 of the base 12. Each end 24 and 26 is provided with a respective inwardly facing indentation 28 and 30 between a respective pair of positioning posts 20 and 22 so as to provide clearance space for gripping the slide 14 to facilitate its placement on and removal from surface 18.

Base 12 has a pair of elongate side rails 32 and 34 which are integral with and upstanting from respective edges 18a and 18b of surface 18 positioned above respective opposing sides 36 and 38 of the base 12. Each side rail 32 and 34 extends generally the entire length of the base between a respective one of each pair of positioning posts 20 and 22. Side rails 32 and 34 upstand from the sides of the slide 14 when the slide is positioned between posts 20 and 22 for preparation of the fluid film. In addition, rails 32 and 34 function as guides during linear movement of the spreader 16.

Each rail 32 and 34 has a respective shoulder 32a and 34a formed in the rail in opposed relationship so as to provide an elongated ramp or bearing formation spaced above the bed 18 and in parallel planar relationship therewith on which spreader 16 is supported during its linear movement required to form the monolayer film on a slide 14. Alternatively, the elongated ramp or bearing formation can be provided in slot formations formed in the inner facing walls of said guide rails, arranged to receive projecting support formations on the spreader. In such a configuration, the slots would be open at opposite ends for accommodating the spreader.

Referring to FIG. 1, surface 18 is provided preferably with an indicator 40 located generally equidistant between rails 32 and 34 and adjacent one of the indentations 30. The indicator 40 designates the location for deposit thereon of the blood sample 13 upon the slide 14. Surface 18 also can be provided with a directional arrow 42. As illustrated in FIG. 3 central recess 19 below the surface 18 is provided for hot stamping of arrow 42 and other artwork without disturbing the flatness of surface 18 on which the slide 14 is supported.

As illustrated in FIG. 3, base 12 is provided with rigidifying means for the surface 18. Illustrative of such means is a plurality of elongate rib members 44 depending from surface 18. Ribs 44 are spaced apart and are parallel along the length of and between the ends 24 and 26 of the base 12. Preferably, ribs 44 extend the entire length of base 12 in order to assure rigidity sufficient to prevent flexing or deformation of surface 18 when substantial downward force is exerted manually on the spreader 16 during smear preparation. Such rigidity of the base is desired in order to provide proper support of the slide 14 which will prevent its breaking or cracking experienced with previous slide bases lacking such structural rigidifying means. While sufficient rigidity of the base could be provided by molding the region below surface 18 in solid or with a single, wide rib, the multiple rib structure substantially reduces the resin consumption and cooling time of the molding cycle.

Additionally, base 12 can be provided with a pair of feet members 46 and 48 located generally below respective sides 36 and 38. As illustrated in FIG. 1, feet 46 and 48 preferably extend the entire length of base 12. Feet 46 and 48 function to maintain base 12 stationary on the work surface (not shown) during the slide preparation. Preferably, feet 46 and 48 are fabricated from a somewhat resilient material, for example a silicone elastomer, which will resist displacement of the base 12 during the spreader movement. As illustrated in FIG. 3, feet 46 and 48 have a "T" configuration including a respective tongue formation 46a and 48a engaged between a respective side 36 and adjacent rib 44, and side 38 and adjacent rib 44b.

Spreader 16 preferably is fabricated by injection molding, for example, from crystal grade polystyrene which enables the spreader to be inexpensive and transparent. As best illustrated in FIGS. 1, 3 and 4, spreader 16 includes a horizontal, planar platform 50 of generally rectangular configuration. The spreader has a pair of gripping members 52 upstanding from opposing sides of platform 50.

As best illustrated in FIGS. 1 and 3, a projection 54 having a generally cylindrical configuration extends laterally outwardly from each respective gripping member 52. Projections 54, which appear like pins or trunnions, are seated on the respective shoulders 32a and 34a and support the front end 56 of the platform 50 above the slide 14. Projections 54 have their axes generally parallel to and spaced above the plane of the platform 50. Thus supported, the front end 56 of the platform 50 will not contact the slide 14. The shoulders 32a and 34a and projections 54 are selectively located at an elevation above the surface 18 and slide 14 so that the bottom edge 62 of the blade 58 is maintained is planar engagement with the slide 14, and platform 50 is horizontal during movement of the spreader. Only blade 58 rides on the slide 14 in the preparation of a smear, as best shown in FIGS. 2 and 3. Accordingly, the entire linear movement of spreader 16 across the slide 14 does not produce grooving in the support surface 18 of base 12 or interruption in the sample smear, even upon slides having a frosted end 14a.

Blade 58 includes an arcuate formation 64 which joins the bottom edge 62 and the platform 50. An arcuate edge 65 formed on the central portion of the rear end 60 of the platform 50 is molded to conform in curvature to the arcuate formation 64 of the blade in order to maintain uniformity of the curvature and thickness of formation 64 during molding of the spreader. Blade 58 is provided with a planar, recessed surface 66 which extends generally parallel to the platform 50 from the bottom edge 62 in the direction generally opposite to the front end 56. The recessed surface 66 provides a clearance space 67 between the blade member 58 and the slide 14 for the formation of a thin film or monolayer of the sample fluid as described hereinafter. The recessed surface 66 intersects a rearwardly inclined surface 68 which forms an angle of approximately 10 to 15 degrees above the horizontal recessed surface 66.

Referring to FIG. 2. To use apparatus 10, a clean slide 14 first is placed on the bed surface 18 of the base 12 between the four positioning posts 20 and 22 so that the unfrosted end of the slide is positioned over the indicator 40. A spreader 16 is placed onto the center of the slide between the guide rails 32, 34 with the projections 54 seated on respective shoulders 32a and 34a. Blade 58 faces, but is spaced from, the indicator 40 as illustrated in the middle position A of the spreader 16 in FIG. 2. A blood sample 13 of approximately 5 to microliters is then deposited on the slide over the indicator 40 using a capillary tube. The spreader 16 is moved manually through the blood deposit with a substantial downward force on handles 52 until the blade 58 of the spreader engages the stop posts 22, as illustrated at the phantom position B of the spreader 16 in FIG. 2. This downward force enables the blade 58 to displace all of the cells from the original location of the sample deposit; also, this initial motion initiates lateral distribution of the blood along the blade 58.

During a brief pause when the spreader 16 is engaged with the post 22, capillary action will spread the blood 13 laterally along the blade 58 so that the clearance spaces 67 between the slide 14 and the recessed surface 66 of the blade will become substantially filled, as best illustrated in FIG. 4. Thereafter, the spreader 16 is moved forward on the slide in the direction indicated by arrow 42 until it engages the posts 20 in the phantom position C illustrated in FIG. 2. The thin, monocellular layer of blood is produced as an even trail behind the blade 58 in conformity with a preferred 0.0026 inch dimension of the clearance space 67. The rails 32 and 34 of the base 12 maintain the lateral alignment of the spreader 16 and the slide 14 in both the initial backward movement and the forward movement of the spreader on the slide 14. The self-lubrication in the compositon of the base 12 promotes smooth traversal of projections 54 on the ramp or bearing formations provided by the shoulders 32a and 34a without excessive wear by reason of repeated use. Although projections 54 have been illustrated as cylindrical pins or trunnions in the preferred embodiment, this configuration is not to be considered exclusive. Thus, the projection 54 may have a slight flat at the point of engagement with the ramp or track. The bed surface 18 of the base is not subjected to grooving or deformation with repeated use.

Minor variations in the size and structural features of cooperating parts and in materials used may occur to the skilled artisan without departing from the crux of the invention, the scope of which is set forth in claims hereto appended.

I claim:

1. Apparatus for preparing a monolayer film of a biological fluid sample, such as blood or the like, on a slide for microscopic analysis, comprising:
   A. a base having opposite extremities and a flat upper surface between said extremities for supporting a slide thereon and a pair of upstanding guide rails extending along opposite side edges of the surface, said guide rails having elongated bearing formations arranged to support a sample spreader thereon during linear movement of the spreader between said guide rails;
   B. a spreader for linear movement between said extremities relative to and engaged with the slide for spreading the sample into a monolayer on the slide comprising:
      i. a generally planar platform having opposing first and second ends,
      ii. projection means protruding laterally from sides of said spreader for engaging said bearing formations for supporting said first platform end above said slide;
      iii. a sample spreading blade member depending from the platform adjacent the second end; and
      iv. means for moving said spreader linearly,
   C. said spreader being constructed and arranged to be positioned for such linear movement between the guide rails along said bearing formations with said blade riding on the slide so that when a sample has been deposited on the slide resting on the said surface, said spreader is movable linearly to enable the blade member to form said monolayer during such linear movement of the spreader between said extremities without engaging said surface.

2. The apparatus as claimed in claim 1 wherein said bearing formations comprise longitudinally extending shoulders formed in said guide rails extending in a common plane parallel to and spaced above said surface.

3. The apparatus as claimed in claim 2 wherein said projection means comprise trunnion formations extending from respective sides of said spreader.

4. The apparatus as claimed in claim 2 wherein said shoulder formations are exposed below the top extremity of said guide rails to allow placement of said projection means upon said shoulders.

5. The apparatus of claim 2 in which said projection means comprise a pair of laterally protruding pins coaxially oriented relative to the spreader.

6. The apparatus as claimed in claim 1 wherein said base includes rigidifying means depending from said surface to prevent deformation of said surface under downward force exerted upon said spreader during said movement.

7. The apparatus as claimed in claim 6 wherein said rigidifying means comprise at least one rib member depending from said surface.

8. The apparatus as claimed in claim 6 wherein said rigidifying means comprise a plurality of spaced apart rib members extending across a substantial part of the length of said base.

9. The apparatus as claimed in claim 1 wherein said guide rails are spaced apart selectively relative to the witdth of the spreader so as to maintain desired alignment of the spreader and the slide.

10. The apparatus as claimed in claim 1 wherein said means for moving said spreader comprise a pair of hand members upstanting from said platform for manually gripping said spreader.

* * * * *